United States Patent [19]
Nacson

[11] Patent Number: 5,426,056
[45] Date of Patent: Jun. 20, 1995

[54] SURFACE IONIZATION DETECTOR FOR DETECTING TRACE AMOUNTS OF ORGANIC MOLECULES

[76] Inventor: Sabatino Nacson, 623 Finch Avenue West, Apartment #610, Willowdale, Ontario, Canada, M2R-3V4

[21] Appl. No.: 116,196

[22] Filed: Sep. 3, 1993

[51] Int. Cl.[6] ................... G01N 30/62; G01N 30/64; G01N 33/15; G01N 33/94

[52] U.S. Cl. ................................ 436/91; 436/96; 436/153; 436/161; 436/816; 436/901; 422/80; 422/82.01; 422/82.02; 422/89; 422/90; 73/23.4; 250/281; 250/283; 250/389; 324/464; 324/468; 324/470

[58] Field of Search ............ 436/91, 92, 96, 98, 436/104, 110–112, 124, 139, 140, 153, 161, 901, 816, 817; 422/80, 82.01, 82.02, 89, 90; 73/23.4, 23.41, 23.42; 250/281, 282, 283, 389; 324/464, 468, 470

[56] References Cited

U.S. PATENT DOCUMENTS 4,622,305  11/1986  Patterson .................... 436/103

OTHER PUBLICATIONS

Surface Ionization Mass Spectrometry of Organic Compounds . . . T. Fujii & T. Kitai, 1986, pp. 129–140.
Surface Ionization Detector for Gas Chromatography: Characteristics . . . H. Arimoto & T. Fujii, Jun. 1991, pp. 415–422.
Mass Spectrometric Studies on the Response Mechanism of . . . T. Fujii, H. Jimba, H. Arimoto, Jan. 15, 1992, pp. 107–111.
High–Performance Emitters for Use in a Surface Ionization . . . T. Fujii, H. Arimoto, 1986, 375–382.

*Primary Examiner*—David A. Redding
*Attorney, Agent, or Firm*—Sim & McBurney

[57] ABSTRACT

A surface ionization detector for detecting organic molecules such as illicit drugs and non-organo-nitrate explosives includes a heated surface and a collector electrode. A sample containing trace amounts of the organic molecules in ambient air is directed over the heated surface maintained at a temperature in the range of 500° C. to 800° C., thereby causing the molecules to decompose into fragments. A polarization voltage between 18 V and 24 V is applied to ionize the fragments which are then collected by the collector electrode. An electrometer connected to the collector electrode measures the current and a change in the current indicates the presence of ionized fragments, and thereby indicates the presence of the organic molecules. The temperature of the heated surface and the polarization voltage are optimized for detection of particular organic molecules.

15 Claims, 13 Drawing Sheets

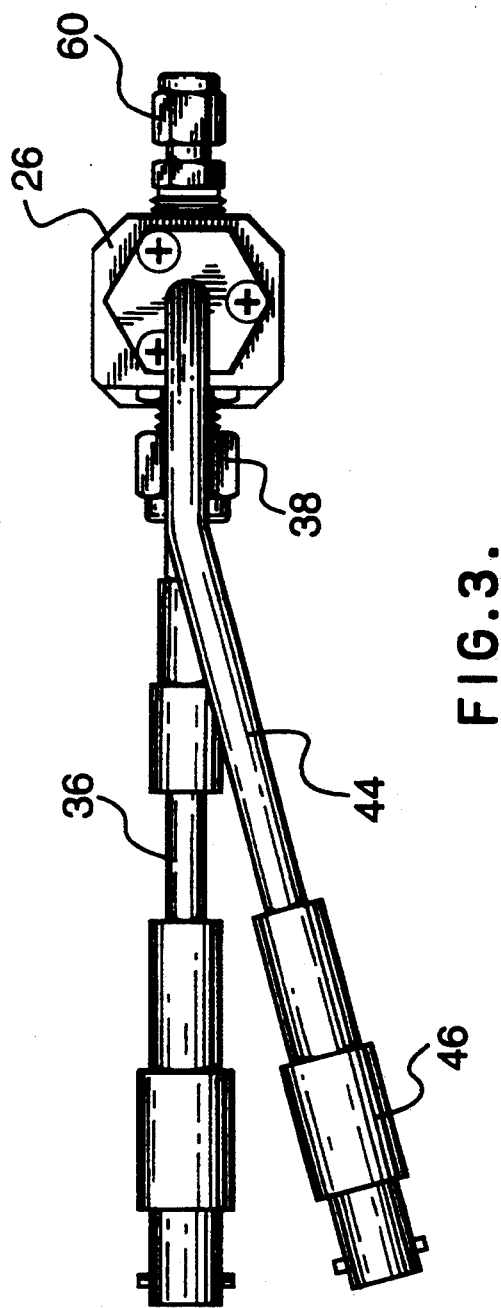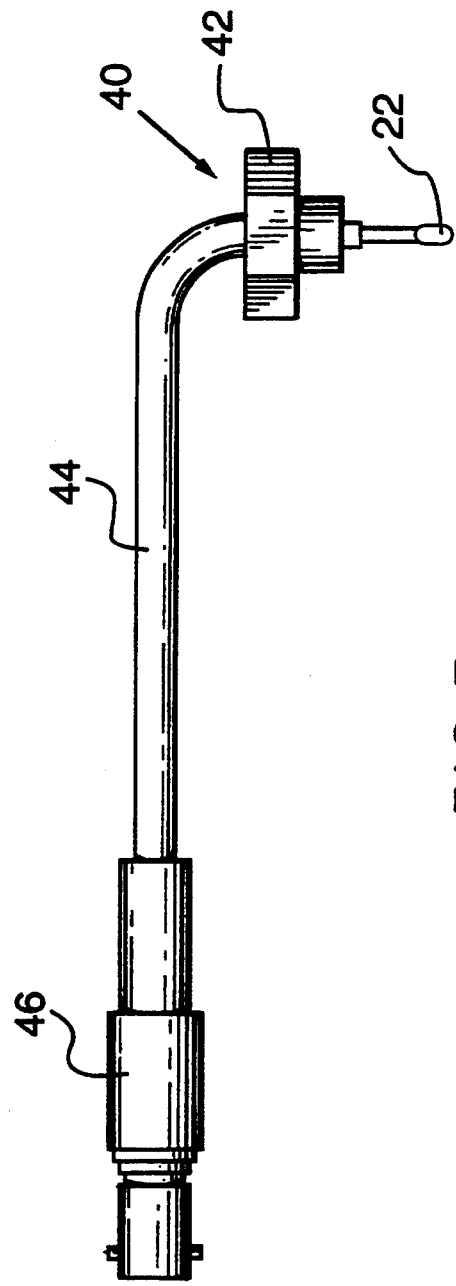

SURFACE IONIZATION DETECTOR FOR DETECTING TRACE AMOUNTS OF ORGANIC MOLECULES

FIELD OF THE INVENTION

The present invention relates generally to an apparatus and method for detecting trace amounts of organic molecules, and more particularly to a surface ionization detector (henceforth to be designated SID, for brevity), that uses ambient air as the carrier gas and which may advantageously, be employed for detecting illicit drugs.

BACKGROUND OF THE INVENTION

The worldwide problem of trafficking of illicit drugs continues despite attempts by enforcement authorities to minimize or eliminate such trafficking. Drug enforcement techniques have become more sophisticated, but traffickers have responded by developing ways to get around presently available enforcement techniques.

One particular area of interest for enforcement agencies is the importation into a country of illicit drugs. Drugs which are transported by air, surface, or vessel are typically concealed by the trafficker in sealed packages, carried on his/her person, in luggage, or in shipments of legitimate cargo. Enforcement agencies are, therefore, in need of a quick and easy-to-use apparatus and method to detect trace amounts of the illicit drugs so that they may be apprehended and seized before entering the country.

Illicit drugs have generally low vapour pressures. They also have another similar characteristic, in that they are often transported in the form of fine granules. These granules are relatively adhering substances. Thus, trace amounts of these granules (particulates) are often present on the clothes of the individuals who have handled the substances, or on the outside of the luggage, or other container in which the illicit drugs are being transported.

Apparatus and methods to detect trace amounts of illicit drugs have been developed over the past decade.

These detection means have been variously based on the use of mass spectrometry (e.g. the work of Sciex, as embodied in U.K. Patent GB 2,162,944B) ion-mobility spectrometry (e.g. the work of Barringer Research Inc., as embodied in the paper entitled "The Detection of Drugs" by John Davies, in Modern Security Systems—A Collection of Papers Presented during International Seminar Held in New Delhi, October, 1989, published by Central Industrial Security Force, New Delhi) and gas chromatography, using a thermionic (nitrogen-phosphorous) ionization detector (TID) as embodied in the article "Portable Trace Narcotics Detector for Field Use", by L. Elias and A. H. Lawrence, Canadian Journal of Spectroscopy, Vol. 32, No. 2, 1987.

Each of these detection means has its intrinsic advantages and disadvantages. For example, mass spectrometry is highly sensitive and discriminating, but ponderous, expensive and difficult to maintain. Ion-mobility spectrometry is sensitive and discriminating, but prone to interferences and contamination and somewhat weighty. GC-TID is sensitive and of reasonable weight and maintenance, but requires the use of a special $H_2/N_2$ mixture as carrier gas, and this is not always readily obtainable.

Typically, methods for detecting trace amounts of illicit drugs will include at least three major steps: 1) collection of a sample of particulates, 2) preconditioning of the sample to release vapours characteristic of the illicit drugs, and 3) analysis of the vapours so released, thereby identifying the substances in the sample and determining the amounts present.

The analysis step may entail the use of gas chromatography, ion mobility or mass spectroscopy. We have found the former to be particularly useful for this purpose. The gas chromatograph may be of the "packed column" type or the capillary column type. The latter is preferable as it makes the overall system smaller and more compact. It is well known that the gas chromatograph's column is used to separate the various constituents of the sample based on their respective retention times in the column. A final detector is included in the gas chromatograph to indicate when the individual constituents of interest of the sample exit the gas chromatograph's column. The traditional final detector for the gas chromatograph may be an electron capture detector, a photo ionization detector, a thermionic detector or other suitable detector, depending on the target constituents of interest.

One requirement for using gas chromatography and its associated detector is that a carrier gas must be used. First the sample is vaporized, and the vapour is injected into the flow of carrier gas, which in turn flows through the column of the gas chromatograph and through the detector. The carrier gas, therefore, has to be clean, in the sense that it is free of the substances to be detected, and chosen so that it does not cause any interference with the detection of those substances. Until now, carrier gases have included chemically inert gases, such as helium and argon, or relatively inert gases, such as nitrogen. As well, depending on the type of detector used, mixtures of inert gases with hydrogen may also be used.

For the detection of illicit drugs, particularly cocaine and heroin, thermionic detectors (e.g. Ref. U.S. Pat. No. 4,622,305, Paul L. Patterson, inventor), used with gas chromatographs have proven useful. However, they require a special hydrogen/nitrogen gas mixture as the carrier gas. The cost and availability of this hydrogen/nitrogen mixture and the uncertainties involved in its use and maintenance limit the practical usefulness of thermionic detectors and the portability of the apparatus as a whole. Accordingly, it would be desirable to have a detector that, in conjunction with a gas chromatograph, did not require a hydrogen/nitrogen mixture or other special gas as a carrier gas. A detector that can be used when ambient air is used as the carrier gas is highly preferable.

SUMMARY OF THE INVENTION

It is an objective of this invention to provide a sensitive and discriminating detector of substances having organic molecules, such as illicit drugs, which can be used with ambient air as a carrier gas. This detector may be used with a gas chromatograph column for high specificity, or by itself, as a light weight, portable detector for rapid use in a variety of search scenarios. Furthermore, according to an important aspect of the invention, the detector is a surface ionization detector (SID).

The present invention provides a surface ionization detector (SID) for use alone, or in association with a gas chromatograph (for higher specificity) to analyze samples containing trace amounts of substances having organic molecules such as illicit drugs and certain explosives. The SID of the present invention is adapted for use with a gas chromatograph that uses ambient air as the carrier gas, rather than a specific gas such as nitrogen gas or hydrogen/nitrogen gas mixture. The ambient air may be scrubbed prior to use so as to remove water vapour, organic contaminants and particulate matter from the air. Operating the gas chromatograph and SID using scrubbed ambient air as the carrier gas is also referred to in this disclosure as using "zero air" carrier gas.

Surface ionization detectors are not unknown, although they are, as yet, little employed in practice. Pertinent references to them are as follows:

1. Toshihiro Fujii and Hiromi Ariomoto; High Performance Emitters for Use in a Surface Ionization Detector for Gas Chromatography, Journal of Chromatography, 355 (1986), p. 375–382.
2. Hiromi Ariomoto and Toshihiro Fujii; Surface Ionization Detector for Gas Chromatography Characteristics and Applications to Organic Substances, Analytical Sciences, Vol. 7, June, 1991, p. 415–422, and
3. Toshihiro Fujii and Hitoshi Jimba; Mass Spectrometric Studies on the Response Mechanism of Surface Ionization Detectors for Gas Chromatography Analytical Chem. 1990, Vol. 62, p. 107–111.

However, none of these references teach the advantageous application of SID detectors to the detection of illicit drugs, and none teach that zero air may be effectively used as a carrier gas, rather than helium, nitrogen or argon (possibly mixed with air).

We have found that, when operated under certain conditions, the SID provides a highly sensitive and relatively selective detector for the more common illicit drugs, including cocaine, heroin and THC. Its selectivity allows it to be used as a rapid, portable, general purpose, illicit drug detector, with an acceptable level of interferences from other substances, or as a detector for a gas chromatograph, for greater specificity.

In addition, we have found that the intrinsic SID sensitivity is so high for these drugs that zero air may be used satisfactorily as a carrier gas, thus avoiding the inconvenience, weight and cost of carrying cylinders of special gases.

BRIEF DESCRIPTION OF THE DRAWINGS

One embodiment of the present invention is shown in the accompanying drawings, in which:

FIG. 3 is a top view of the SID of FIG. 2;

FIG. 5 is a side view of the platinum wire and its connector assembly;

DETAILED DESCRIPTION OF THE PREFERRED EMBODIMENT

Figure 1:
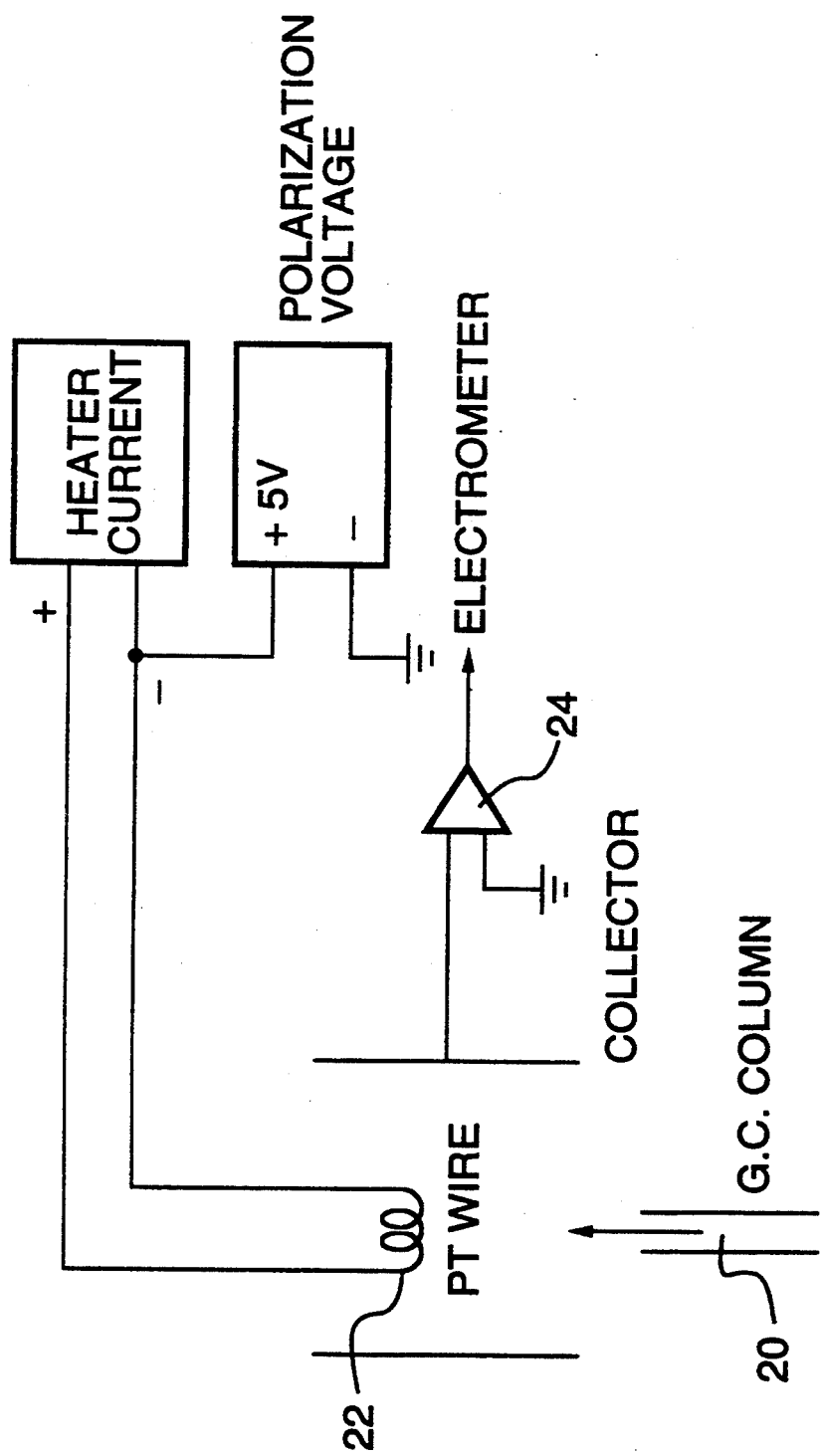
FIG. 1 is a schematic diagram of the SID of the present invention.

Referring to FIG. 1, there is shown a schematic diagram of a typical surface ionization detector (SID). In accordance with the present invention, the sample to be analyzed may be first separated in the column 20 (partially shown) of a gas chromatograph using scrubbed ambient air as the carrier gas. The separated constituents of the sample and the carrier gas exit the column of the gas chromatograph and enter the SID for final detection.

The SID comprises a platinum wire 22 through which a current is passed to heat it up to a desired temperature. As the sample and carrier gas exit the column, they pass over the heated surface of the platinum wire 22. Molecules of organic compounds, such as illicit drugs present in the sample decompose upon contact with the hot surface of the platinum wire 22, to smaller, ionizable fragments, and the fragments are ionized. A voltage is applied and the ionization current due to the fragments is then measured by use of an electrometer 24. When the gases passing over the platinum wire 22 are inert and do not contain molecules of organic substances such as illicit drugs, no decomposition takes place and the current measured by the electrometer 24 remains constant. Changes in the ionization current measured by the electrometer 24, thereby indicates the presence of the illicit drugs.

Although not wishing to be bound by any theory, it is believed that the operation of the SID is as follows. Basically, the SID works on the principle that organic compounds are ionized when interacted with a heated, appropriately activated solid surface. Molecules of illicit drugs, such as cocaine or heroin, present in the gas exiting the gas chromatograph's column 20, pass over the heated surface of the platinum wire 22. This causes the molecules to decompose to smaller, easily ionizable fragments. The decomposition process may be represented by the following equation:

$$\text{drug molecule} \xrightarrow[500-800\ C.]{\text{surface}} \text{fragment}^+ + e^- \tag{1}$$

The polarization or ionization current for the fragment$^+$ is determined by the efficiency of the formation of the fragment on the platinum wire's surface and also by the ionization efficiency, which is determined semi-quantitatively by the known Saha-Langmuir equation (2).

$$\alpha = N^+/N_0 = g_+/g_0\ exp\ (\Phi - IE/KT) \tag{2}$$

where:
 $N^+$ is the number of ions leaving the surface per unit area;
 $N_0$ is the number of neutral species emitted from the same surface in this time;
 $\Phi$ is the work function of the surface on which ionization occurs at temperature T;

K is the Boltzman constant;

IE is the ionization energy of the emitting chemical species; and $g^+/g_o$ is the ratio of the statistical weights of the ions and the neutral species.

The Saha-Langmuir equation (2) is based on the assumption that thermal and charge equilibria are established between the species on the surface and the surface material itself. Thus, equation (2) describes the temperature dependence of the ionization degree.

As is well known, organic molecules will decompose into fragments which, generally, have lower ionization energies (IE) than the molecules themselves, thereby resulting in more efficient ionization. For a given type of fragment formed on the surface, the resulting positive thermionic emission current is dependent on the surface temperature (T). This dependency may be described as follows:

$$I_S(T) = n Y_S(T) B_S(T) \quad (3)$$

where $I_S$ is the thermionic emission current

T is the surface temperature n is the number of molecules $Y_S(T)$ is the yield of chemical reactions on the surface $B_S(T)$ is the ionization efficiency Using the Saha-Langmuir equation (2), the ionization efficiency $B_S(T)$ may, therefore, be expressed as:

$$B_S(T) = \frac{1}{1 + (g^0/g^+)\exp\frac{(IE - \phi)}{KT}} \quad (4)$$

Equation (4) indicates that the yield ($Y_S(T)$) and the work function ($\Phi$) must be high in order for the ionization efficiency to be high. As well, equation (4) shows that the ionization efficiency, and hence the surface ionization process as a whole, is very specific to particular molecules since it is strongly dependent on the ionization energy (IE) of the particular species.

Therefore, there are three important parameters in the SID that determine its response to specific molecules: (a) the work function ($\Phi$) of the surface, (b) the operating temperature (T) of the surface, and (c) the chemical composition of the gas environment immediately surrounding the surface.

The work function ($\Phi$) of the surface of the platinum wire 22 can be increased by ensuring that oxygen or other oxidizing gases are present in the SID. Oxidation of the surface of the platinum wire 22 increases the work function, which in turn increases the ionization efficiency as shown in equation (4). In gas chromatographs using a hydrogen/nitrogen gas mixture as the carrier gas, an oxygen-containing gas is introduced into the SID but not in the gas chromatograph's column. But with the SID of the present invention, ambient air is used as the carrier gas, thus a separate input of oxygen-containing gas into the SID is not necessary.

The second parameter, the surface temperature (T) of the platinum wire 22, is determined by the current passing through it. The amount of decomposition occurring on the surface is dependent on the surface temperature, and each type of molecule will have an optimum surface temperature at which maximum decomposition and ionization will occur. In the case of illicit drugs such as cocaine and heroin, the optimum surface temperature has been determined for systems where ambient air is used as the carrier gas. These results are set out more fully below.

Figure 2:
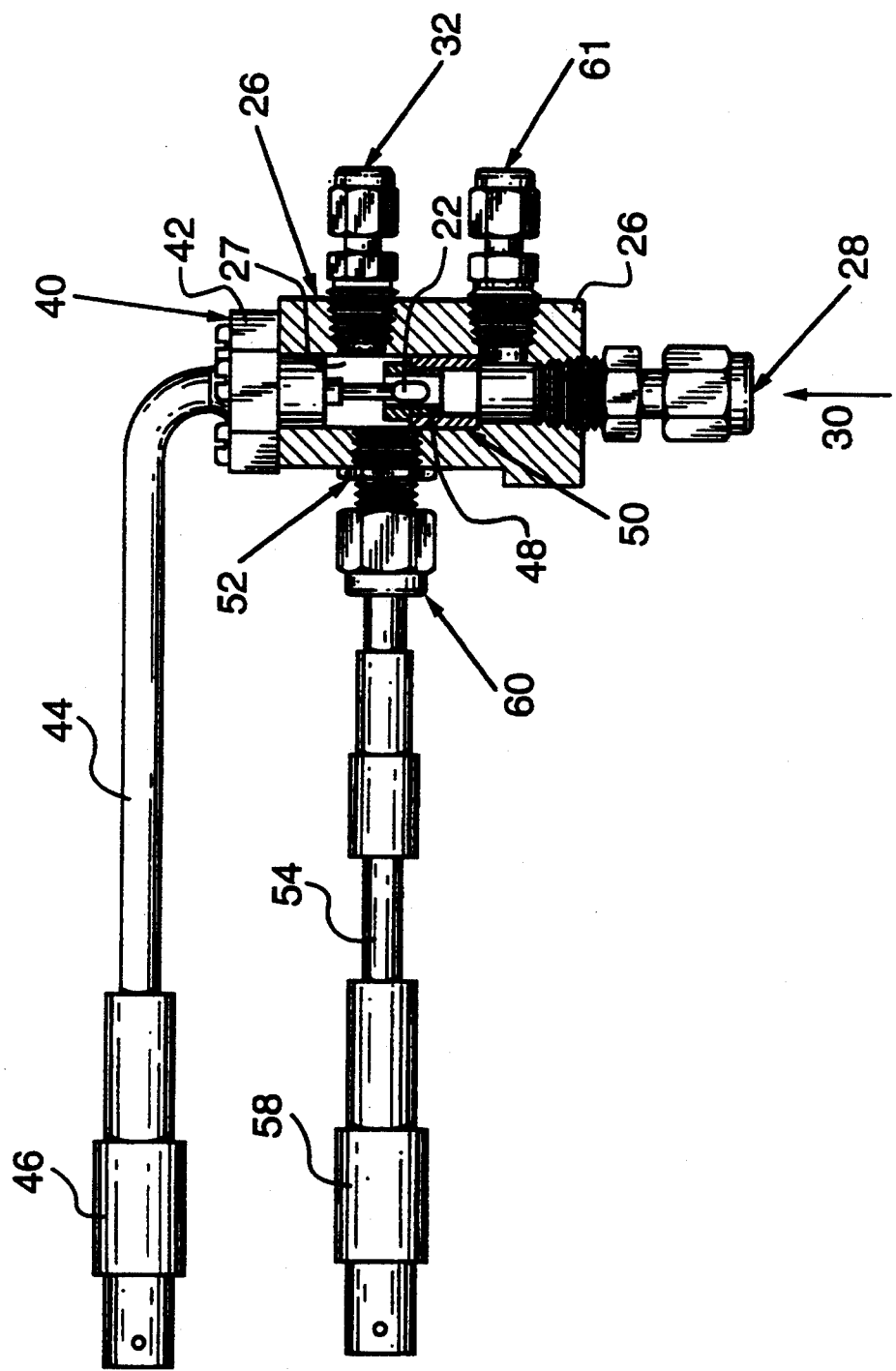
FIG. 2 is a side view of the SID according to a first embodiment of the present invention.
Figure 4:
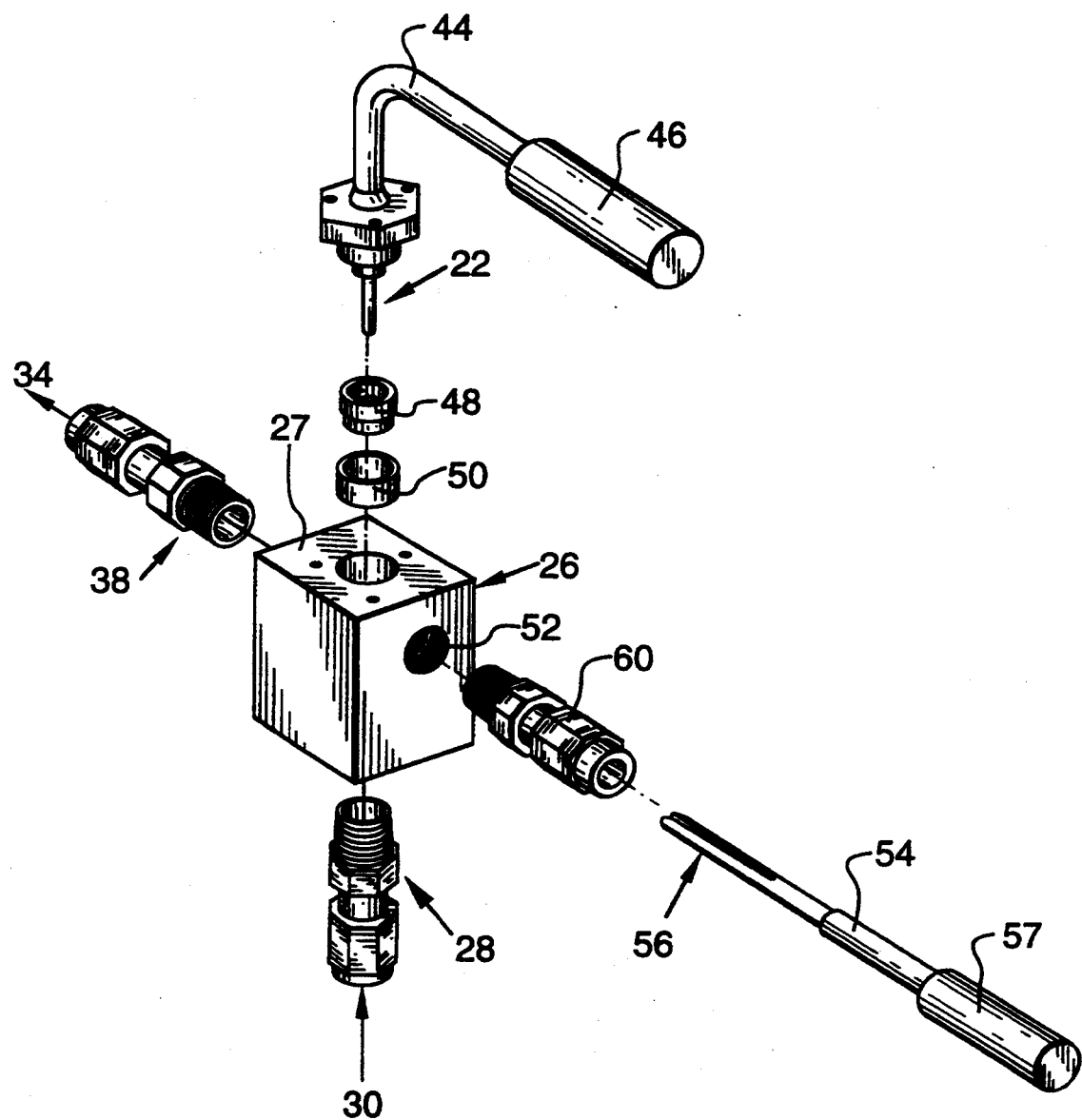
FIG. 4 is an exploded view of the SID according to an alternative embodiment of the present invention.

FIGS. 2 and 3 show in greater detail one embodiment of the SID of the present invention and FIG. 4 shows a second embodiment. Both embodiments include most of the same components, which are described in greater detail as follows. The SID includes a housing portion 26 having a cavity 27 therethrough. The platinum wire 22 is located within the cavity 27. The SID is connected to the column of the gas chromatograph by way of a first connector 28, which is a one eighth inch pipe thread to a one eighth inch swagelock union. The carrier gas and separated sample from the column enter the SID through connector 28 in the direction of arrow 30.

An exhaust port 32 is provided on one side of the SID. After the detection of the sample, the carrier gas and sample are exhausted through this port 32 in the direction of arrow 34.

The platinum wire 22 is located within cavity 27 and held in place using the platinum wire connector assembly 40. The connector assembly 40 includes means 42 for holding the platinum wire in place. The platinum wire is electrically connected to cable 44, which in turn is electrically coupled to a connector 46. The connector 46 leads to a power supply (not shown) which provides the polarizing voltage for the platinum wire 22.

The connecting assembly 40 further includes the collector electrode 48 and a ceramic insulator 50. When the platinum wire assembly is in place in cavity 27, the collector electrode surrounds the platinum wire, but does not contact with it. The ceramic insulator 50 in turn surrounds the collector electrode and electrically insulates the collector electrode 48 from the SID's housing 26.

The collector electrode 48 is connected to an electrometer (not shown) through at least one port.

In the embodiments of FIGS. 2 and 4, the collector electrode 48 is shown connected to the electrometer through one side port only. In this case, the side port 52 allows a cable 54 having a port end 56 to be threaded through side port 52 so that the port end 56 is in electrical contact with collector electrode 48. The cable 54 is further connected to a connector 58 that leads to the electrometer. The cable 54 is secured to the SID through the use of a connector 60, which in the embodiment of FIG. 4 is a one eighth inch pipe thread to a one eighth inch swagelock union.

In the embodiment of FIG. 2 and 3, an optional air inlet port 61 is provided which is not provided in the embodiment of FIG. 4. Air inlet port 61 may be used as an inlet for feeding additional carrier gas to the SID in cases where it is desirable to have a greater gas flowrate in the SID than the gas flowrate in the gas chromatograph column. This typically occurs if a capillary column is used since gas flowrates in such columns are relatively low. Thus, additional carrier gas may be fed to the sample stream to ensure that the gas flowrate in the SID is within the optimum range for the particular organic molecule being detected.

EXAMPLES

A Varian 3400 gas chromatograph equipped with a 3 meter, 0.53 mm ID, 0.5 mm film thickness of MXT-1 capillary column was used. The capillary column was operated isothermally at 170° C. The injector port of the gas chromatograph was maintained at 250° C., whereas the surface ionization detector (SID) was operated at a constant 300° C.

The effects of the following parameters on the SID's response to illicit drugs were evaluated: 1) carrier gas type, 2) carrier gas flowrate, 3) polarization voltage and 4) platinum wire surface temperature (measured by way of the current passed through the wire). As well, the selectivity of the SID for illicit drugs and other selected organic compounds was determined.

Figure 6:
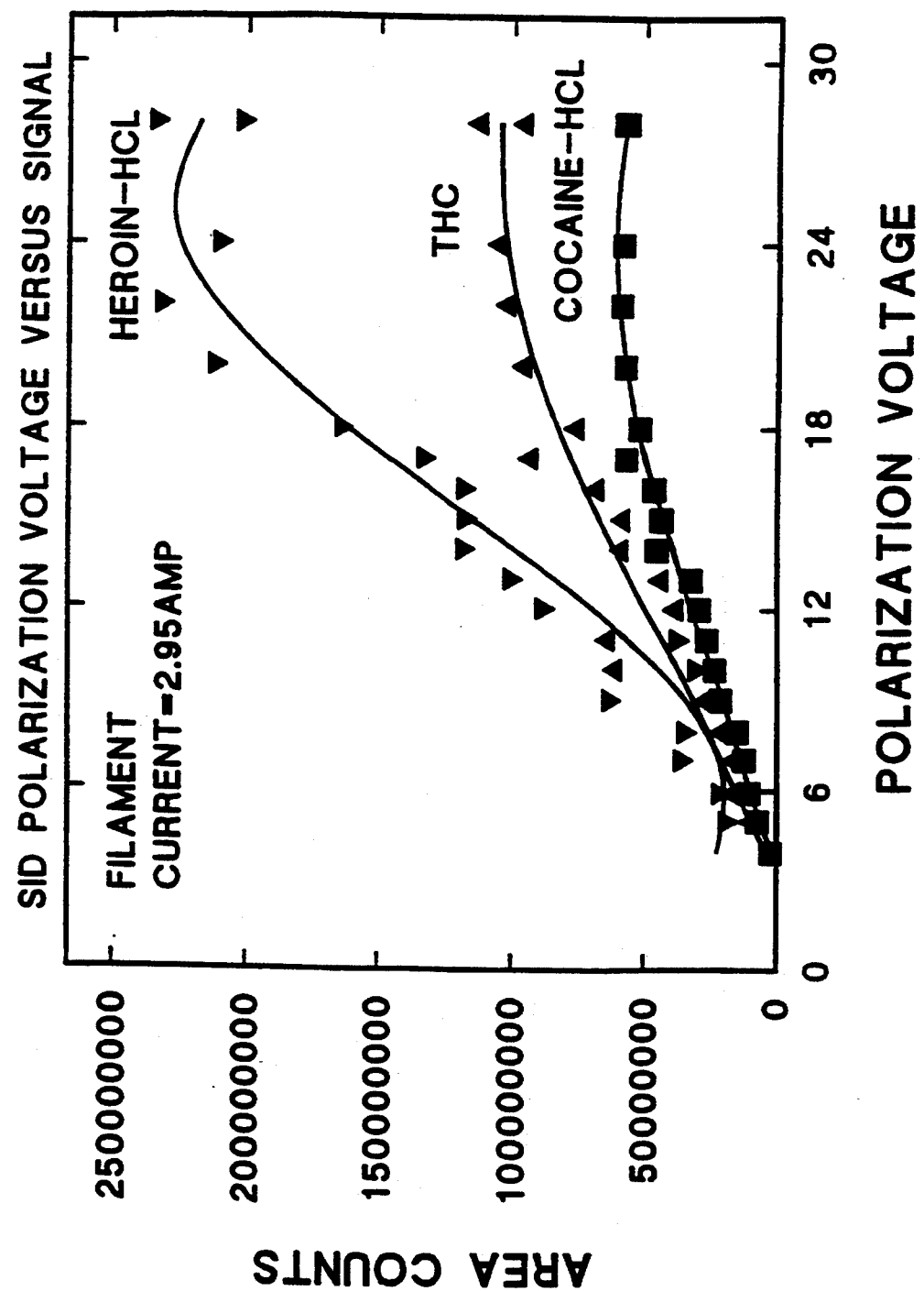
FIG. 6 shows the relationship of the SID polarization voltage versus signal.

The optimum polarization voltage on the SID response was determined for cocaine hydrochloride (cocaine-HCl), tetrahydrocannabinol (THC) and heroin hydrochloride (heroin-HCl). FIG. 6 presents the results of this study and shows that the optimum voltage is in the range of about 18 V to about 24 V DC. Above that level there appears to be no increase in output signal. During the study, the current through the platinum wire was held constant at 2.95 Amp.

The preferred polarization is thus in the range of 18 to 24 V DC. The drift speed of the ionized fragments produced on the surface of the platinum filament is proportional to the intensity of the electric drift field E.

$$V = KE \quad (5)$$

where
K is the linear ion movement or mobility
Vd is the drift speed
S is the electric field The drift time t between the filament surface and the collector electrode is:

$$t = d/KE \quad (6)$$

where
d is the distance

The drift time of an ion in the SID detector can be expressed for any temperature or pressure as:

$$t = \frac{273 Pd}{760 k_0 TE} \quad (7)$$

where
$k_0$ is the reduced mobility of the ion
P is the pressure measured in Torr (the SID is operated at atmospheric pressure)
T is the absolute temperature Equation (7) shows that an increase in pressure or a decrease in temperature results in an increase in drift time. By applying the general theory of ion mobility in weak electrical fields based on the kinetic theory of gases, the ion mobility K is formulated as:

$$K = \frac{3e}{16N} \left( \frac{1}{m} + \frac{1}{M} \right)^{\frac{1}{2}} \left( \frac{2\Pi}{kT} \right)^{\frac{1}{2}} \left( \frac{1}{C} \right) \quad (8)$$

where
K is the ionic mobility (m$^2$/Vsec)
N is the density of uncharged drift gas (molecules/CE)
e is the charge of the ion
m is the mass of the ion
M is the mass of the neutral drift gas molecule (air)
k is the Boltzmann constant
T is the absolute temperature
C is the average collisional cross-section From equation (8) it can be seen that the mass of the ion becomes much larger than the mass of the drift gas molecules, thus the mass dependent term of the equation becomes insignificant. Therefore, the mobility of a large ion is controlled by the average collisional cross section of the ion with the neutral drift molecules. As the mass (m) of the ion increases, the ion mobility is smaller for a constant applied electric field. The electric field (V/Cm) is directly proportional to the square root of the mass of the drifting ions.

The geometry of the SID of the present invention allows a very short distance for the ions to travel from the hot filament to the collector electrode. This distance is preferably less than 6 mm, measured from the tip of the filament to the center plate of the electrode.

The preferred polarization voltage range can be expressed in terms of the electric field (E), such that the preferred optimum range in the SID of the present invention is 30 V/cm to 40 V/cm.

Figure 7:
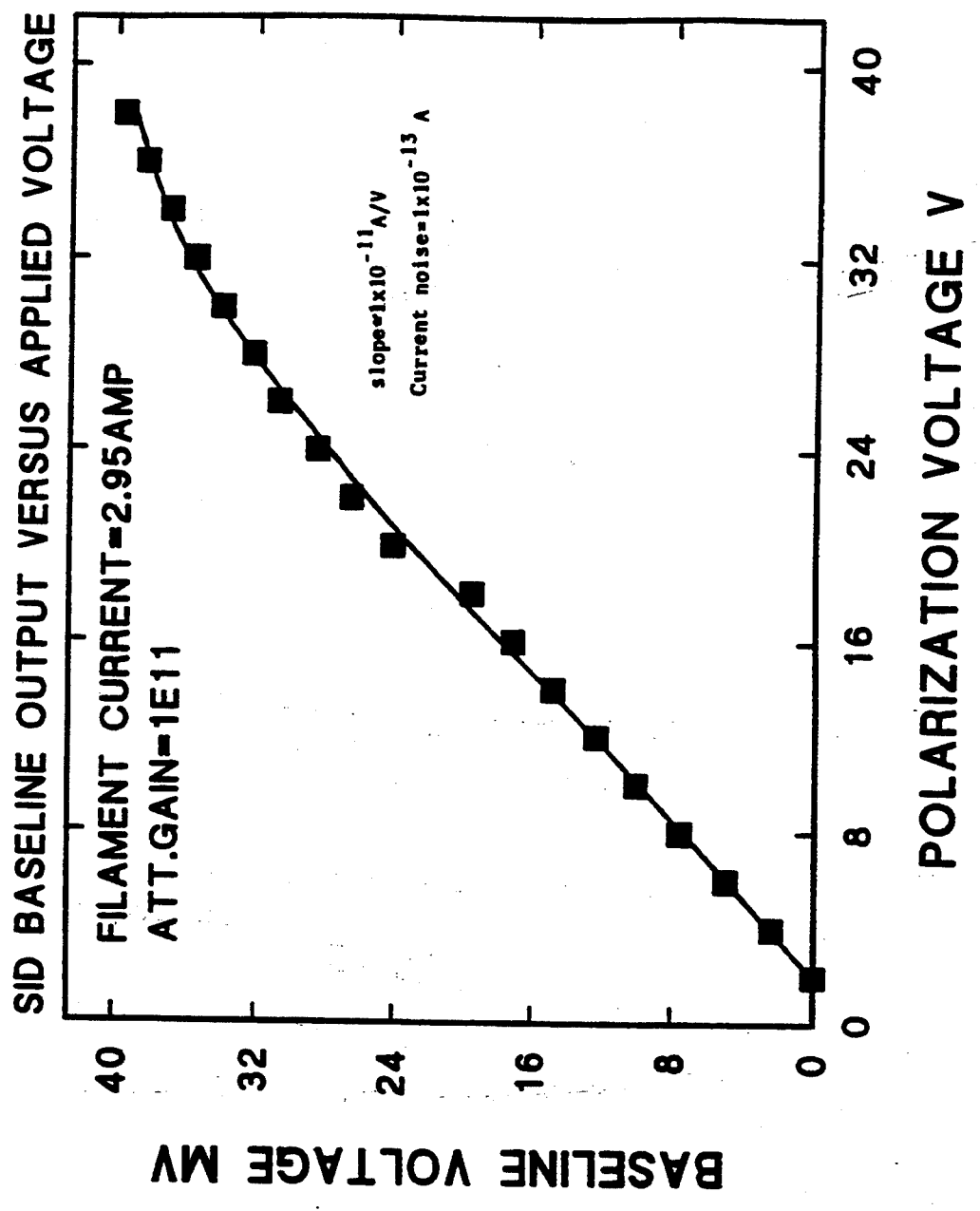
FIG. 7 shows the SID baseline output versus applied voltage.

However, it is found that, as the polarization voltage increased, the background or baseline signal (expressed as mV) increased at the rate of $1 \times 10^{-11}$ Amps per Volt, up to a polarization voltage of 40 V. The relationship between baseline voltage and polarization voltage is illustrated in FIG. 7. Thus the signal/noise decreases progressively for polarization voltages beyond 24 V. The current noise, however, remained unchanged at about $1 \times 10^{-13}$ Amps.

Figure 8:
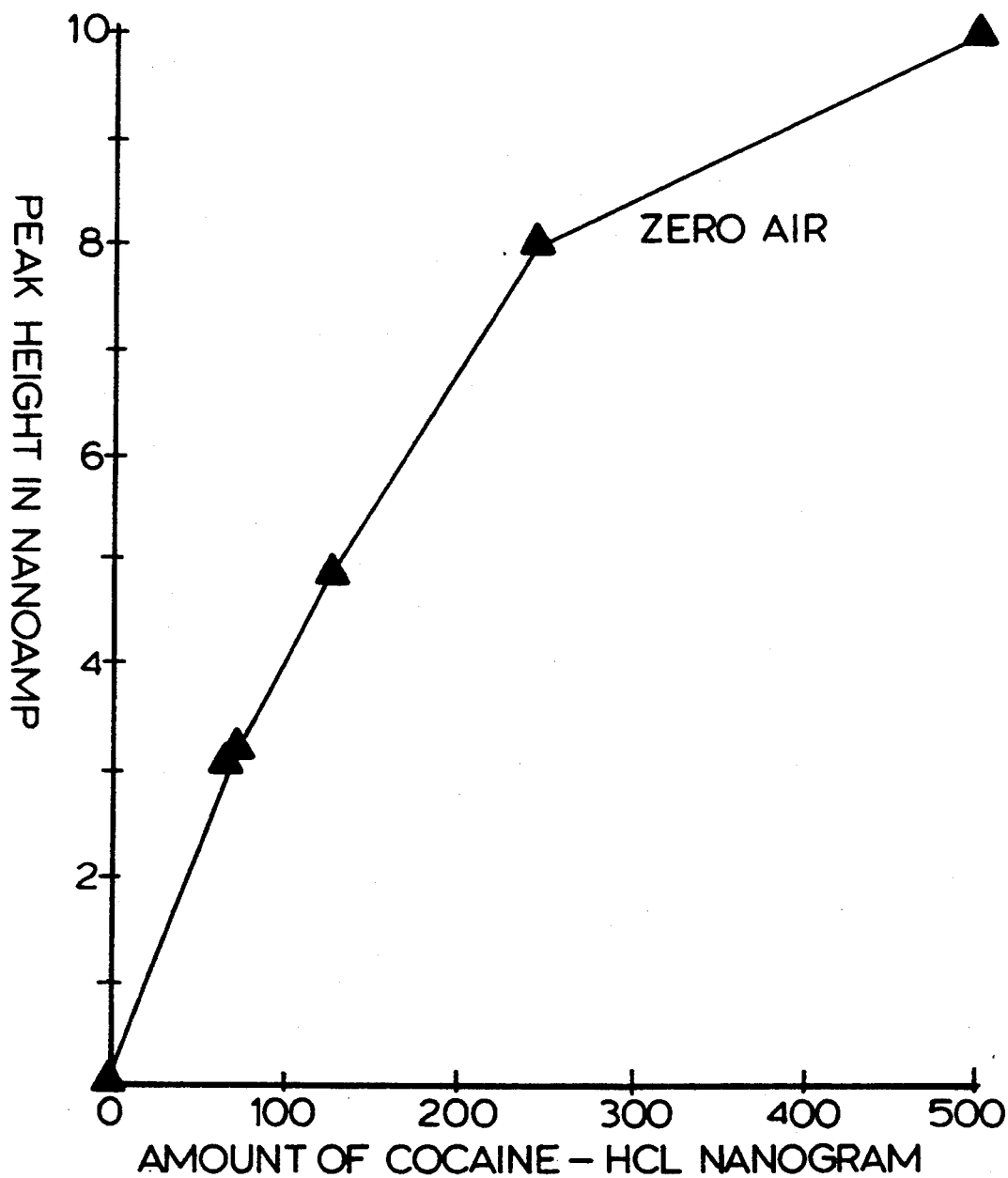
FIG. 8 shows the calibration of the SID for cocaine-HCl under $N_2$ and Zero Air.
Figure 9:
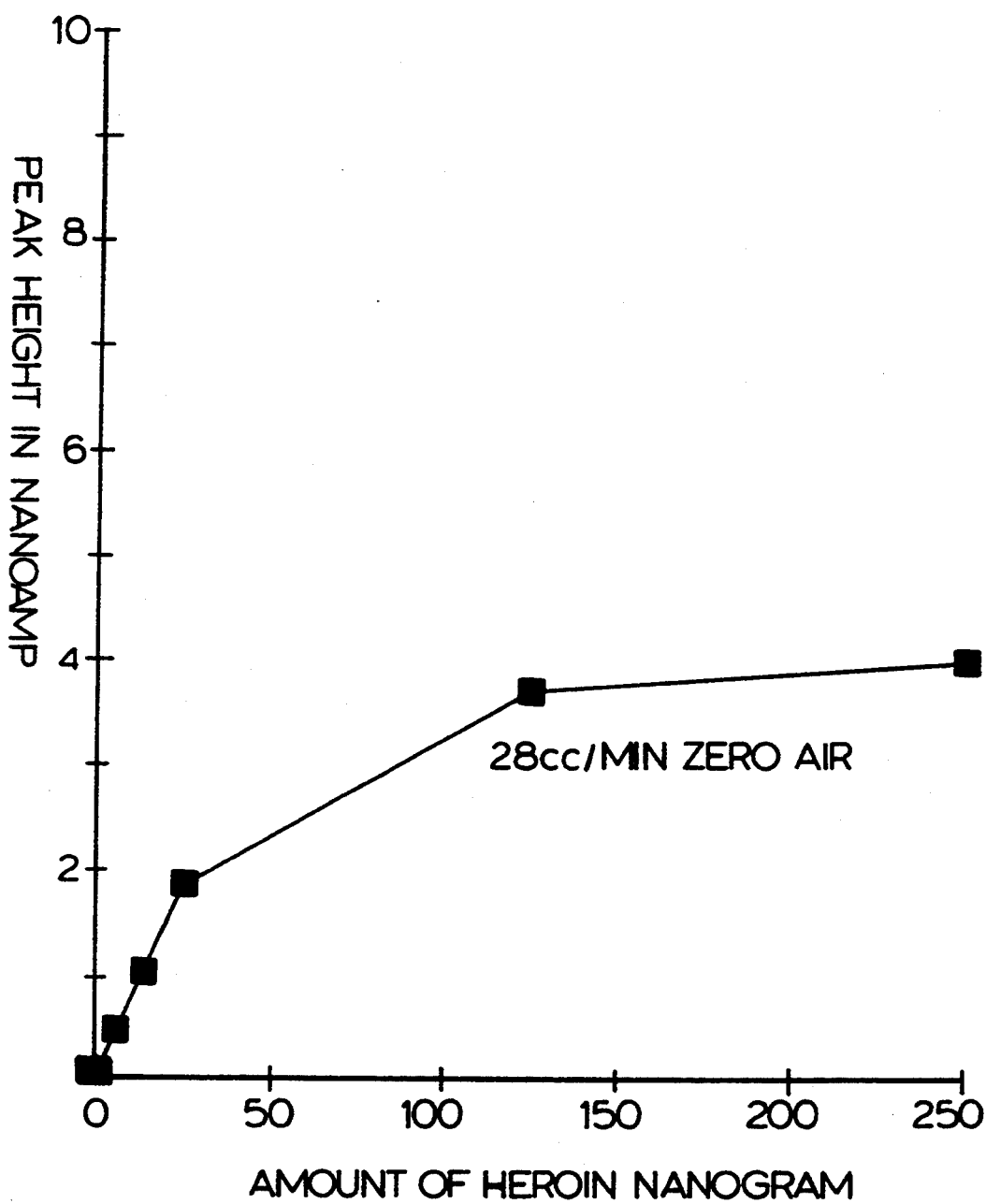
FIG. 9 shows the calibration of the SID for heroin-HCl under $N_2$ and Zero Air.

FIGS. 8 and 9 show the effect of using scrubbed ambient air (referred to as "zero air") and nitrogen gas as the carrier gas with respect to detecting cocaine-HCl and heroin-HCl signals. Whereas it was found that the sensitivity of the SID decreased by about a factor of five for cocaine and about ten for heroin, when the SID operated with zero air, as compared to when nitrogen gas was used as the carrier gas, the signal-to-noise ratio, in the case of 10 ng sample of cocaine-HCl was still found to be better than 1000. In both experiments, all other conditions were kept constant, in particular, the background noise current was stable at about $1 \times 10^{-13}$ Amps in both cases.

Of note, therefore, is that the sensitivity of the SID to illicit drugs under zero air conditions is still in the low nanograms range (the linear regions of the "Zero Air" curve in FIGS. 8 and 9). Thus, operating the SID using zero air conditions still permits the detection of cocaine, THC and heroin in the 1–10 nanogram range.

Figure 10:
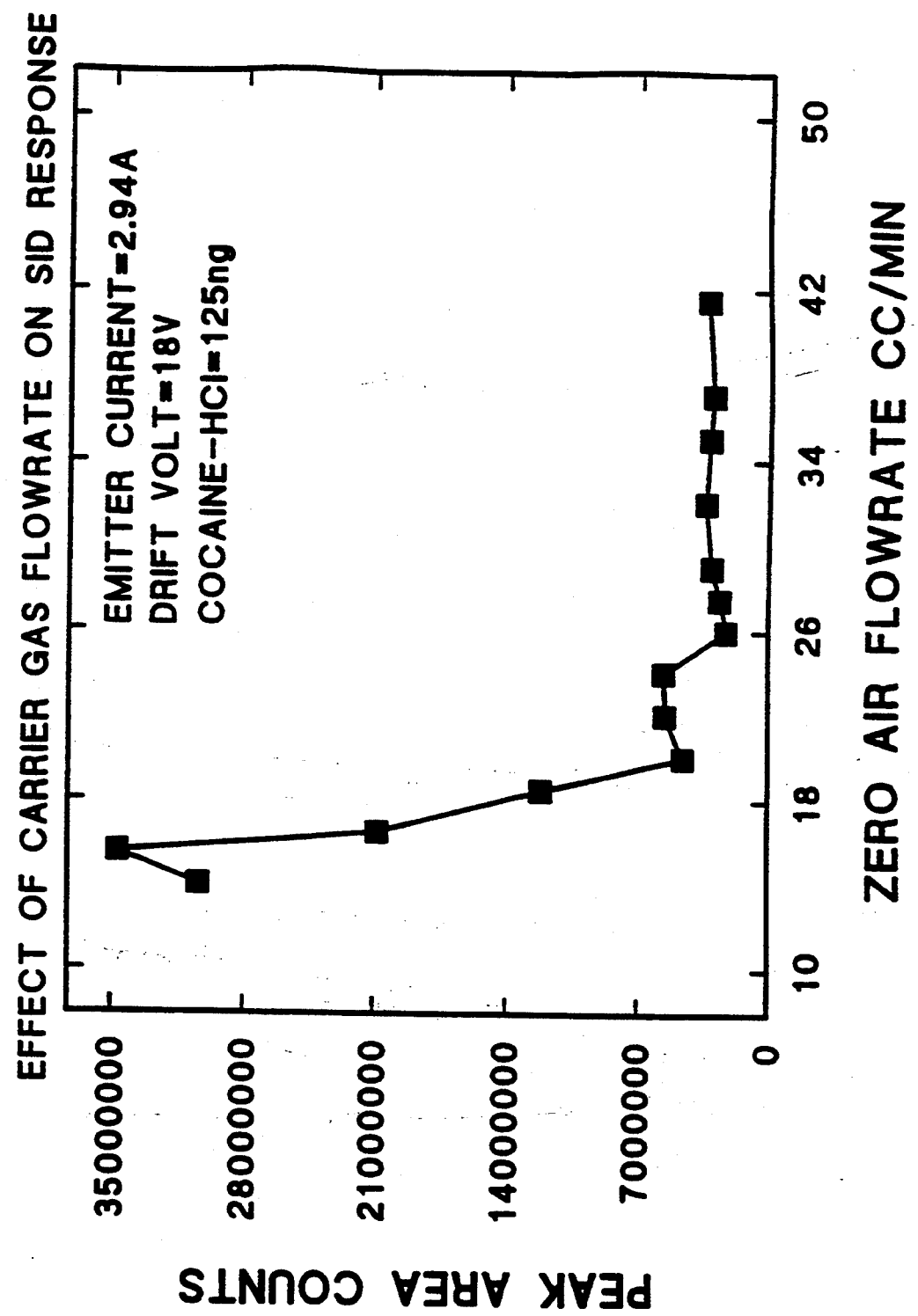
FIG. 10 shows the effect of carrier gas flowrate on SID response.

FIG. 10 illustrates the effect of varying the flowrate of the carrier gas on the response of the SID. In this study, the current through the platinum wire ("emitter current") was kept at 2.94 Amps, the polarization voltage ("drift voltage") at 18 V and a 125 nanogram sample of cocaine-HCl was used. It was found that the response to the cocaine-HCl sample decreased rapidly with a slight increase from 10 cc/min to 20 cc/min in the carrier gas flowrate. Once the flowrate is in the range of about 20 to 100 cc/min, the signal was found to be independent of flowrate.

At the low flowrate regime, high sensitivity is achieved, whereas at the relatively higher flowrates (greater than 30 cc/min) lower sensitivity is achieved due to the dilution effect occurring in the ionization region of the detector. Cooling of the filament at higher flowrates and thereby lower surface ionization temperature may contribute to the lower sensitivity.

The relationship between the platinum wire's temperature and the SID sensitivity was also determined. The platinum wire's temperature is directly dependent on the current flowing through the wire. Thus, by controlling the emitter current, the temperature is controlled.

Figure 11:
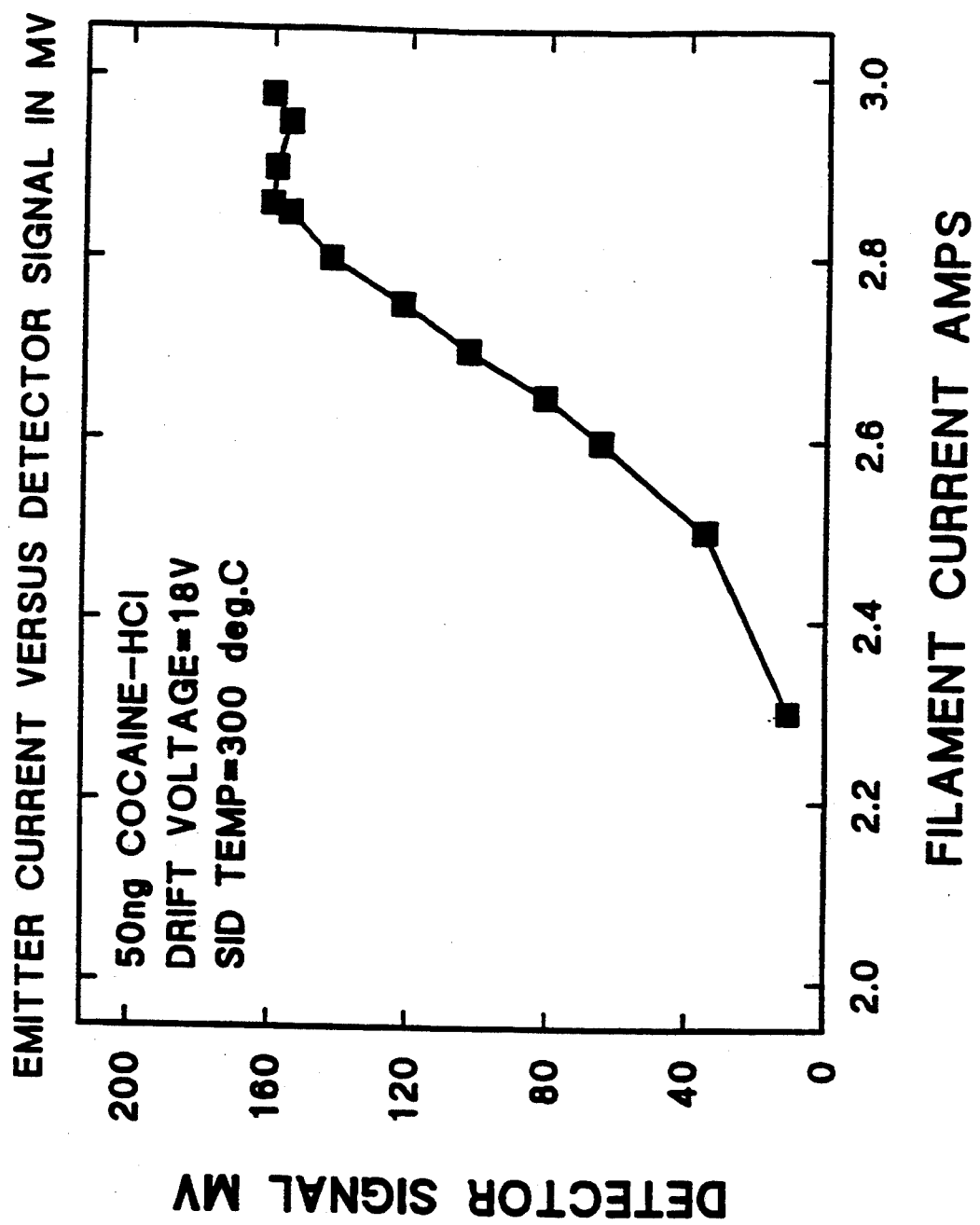
FIG. 11 shows the emitter current versus SID signal.

FIG. 11 shows the results of this study. The SID's sensitivity to a 50 ng sample of cocaine-HCl increased as the emitter current increased, until it became independent of the emitter current at above 2.8 Amps. Similar results (although not presented here) were obtained with heroin-HCl and THC samples.

The platinum wife's temperature can be approximately calculated if the electrical resistance of the platinum wire is known. The wife's resistance is calculated as follows:

$$r_1 = r_0 (1 + 0.00395 T_1) \quad (5)$$

where:
- $r_1$ is the resistance at a particular temperature
- $r_0$ is the resistance at room temperature
- 0.00395 is the temperature resistance coefficient for platinum
- $T_1$ is the difference between the temperature of the wire and room temperature, in °C.

It was found that the approximate temperature of the platinum wire was 580° C. when 5.148 W of power was applied to the wire, and 600° C. when 6.047 W was applied. The average temperature was found to be 593° C. when the current was in the range of 2.8–3.0 Amps.

Figure 12:
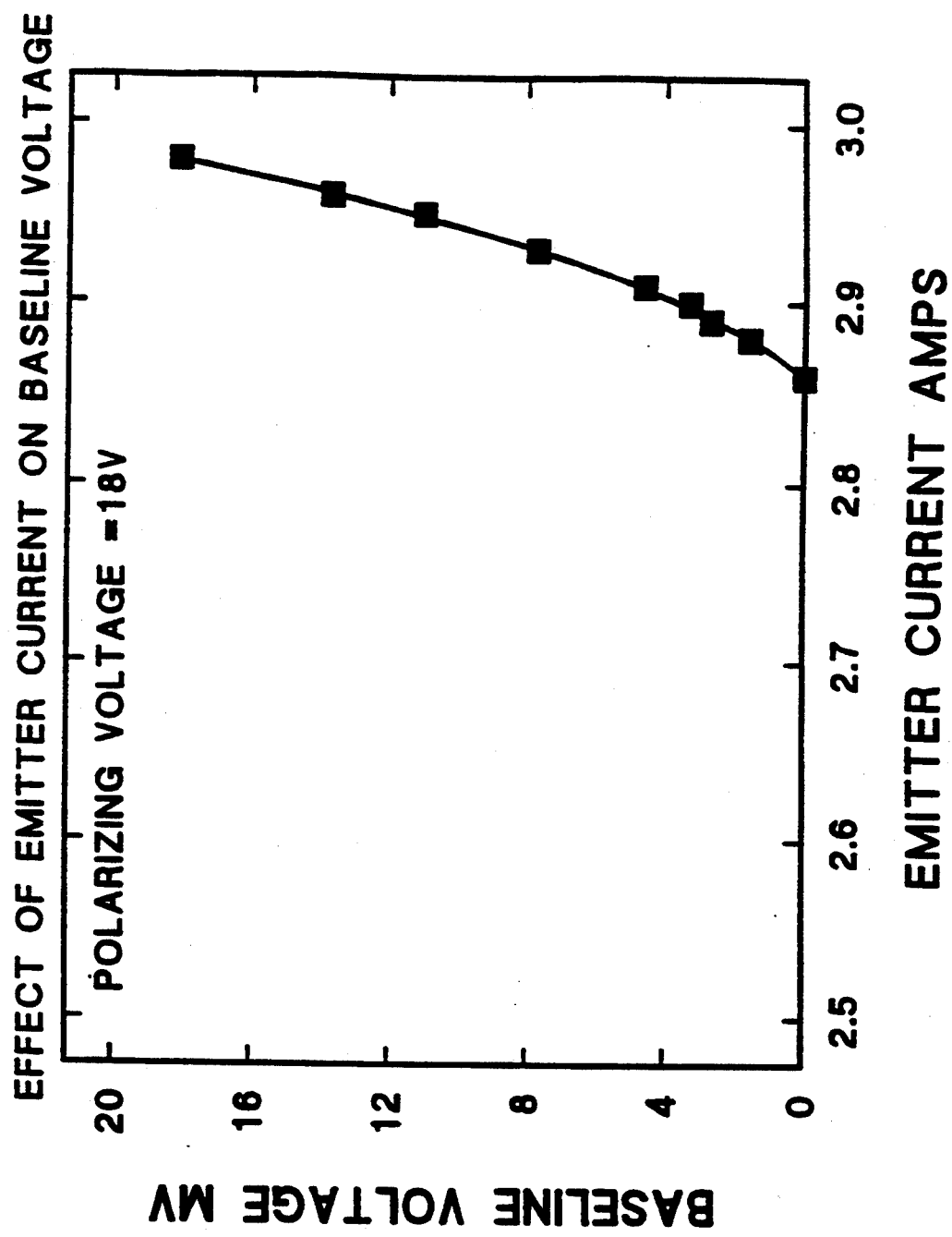
FIG. 12 shows the effect of the emitter current on baseline voltage.

The effect of emitter current on background signal was also determined. FIG. 12 shows that the background signal increased as the emitter current increased. However, the current noise at the highest emitter current remained unchanged at $1 \times 10^{-13}$ Amps.

Figure 13:
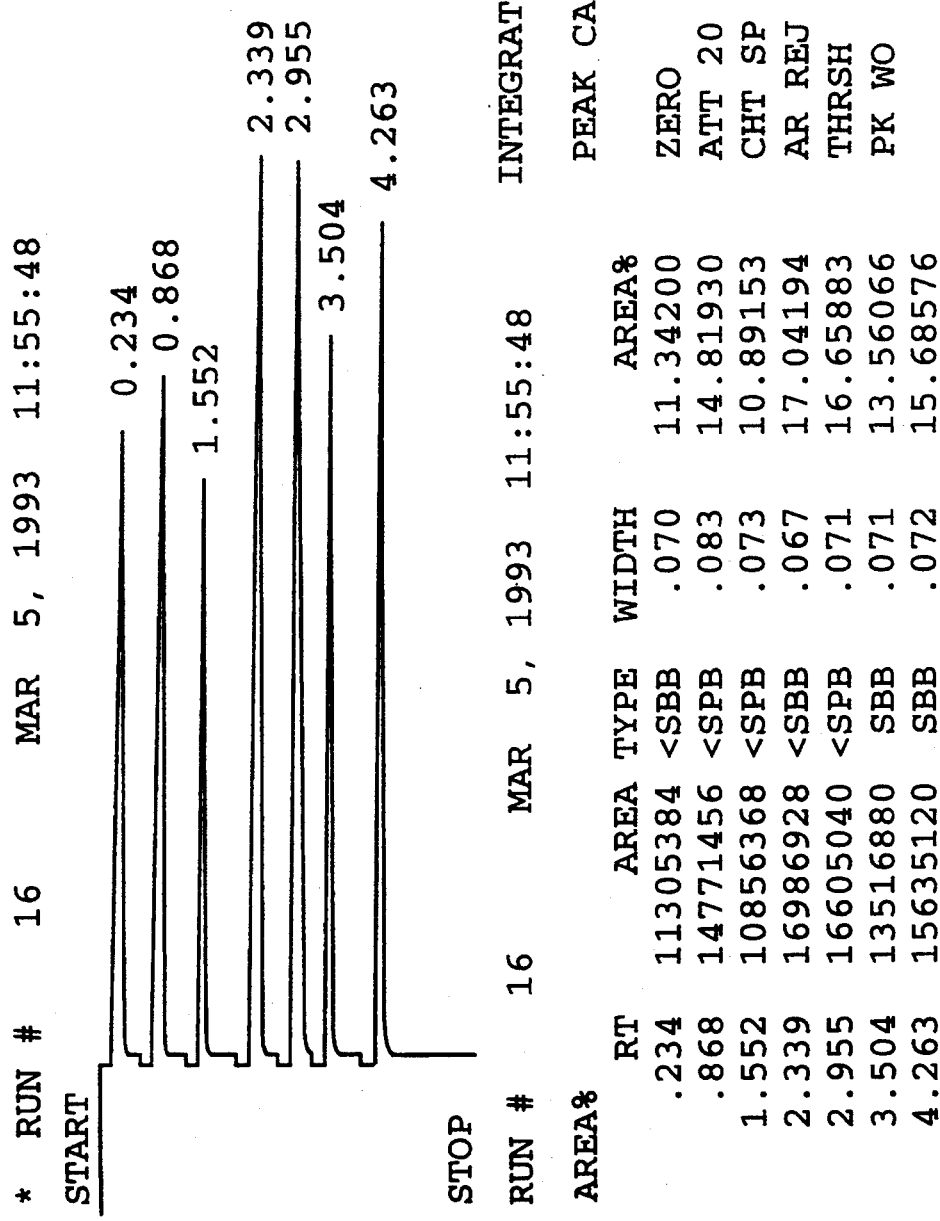
FIG. 13 are chromatographs illustrating the repeatability of the results obtained using the SID of the present invention.

The repeatability of results obtained using the SID of the present invention was also investigated. FIG. 13 shows the chromatograms obtained from 7 separate samples, each sample containing 10 ng of cocaine-HCl in methanol. The carrier gas used was zero air flowing at 29 cc/min, and the gas chromatograph was operated isothermally at 170° C. Baseline stability was quickly achieved after 15 seconds of turning the power on to the SID, whereas optimum signal was reached after 5 minutes of operation. The standard deviation between the samples was determined to be 17%.

Figure 14:
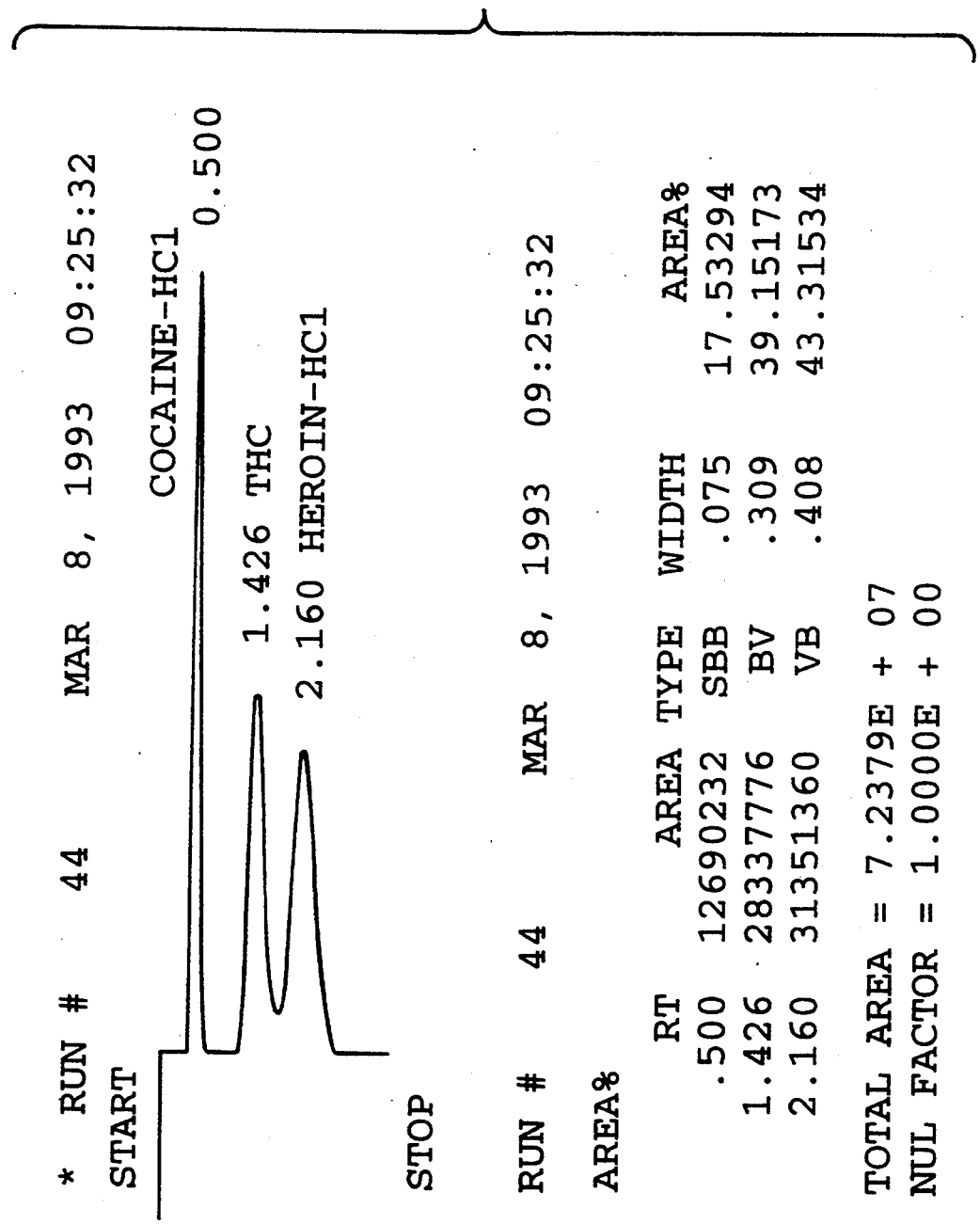
FIG. 14 is a typical chromatogram of a mixture of cocaine, THC and heroin, obtained using the SID of the present invention.

FIG. 14 shows an example of a typical chromatogram of a sample containing a mixture of cocaine, THC and heroin. This chromatogram was obtained using zero air carrier gas flowing at 29 cc/min. The Varian G.C. 3400 injector port was kept at 250° C., the column at 170° C. (isothermal) and the SID temperature at 300° C. The emitter current was maintained at 2.94 Amps and the polarization voltage at 18 V.

The selectivity of the SID for positive ions, and some negative ions, was also investigated. The SID was found to show selectivity to amino containing compounds, such as illicit drugs, but surprisingly, not to some ringbound nitrogen compounds, such as caffeine. This behaviour is significant since the SID of the present invention is, therefore, reliable and useful for detecting illicit drugs, but does not react to certain other compounds that might be expected to interfere.

Table I below shows a partial list of the compounds that can be detected by the SID of the present invention. The SID operating under zero air carrier gas conditions acts as a universal detector which allows efficient ionization of a large number of organic compounds.

TABLE I

| NITROGEN CARRIER GAS | ZERO AIR CARRIER GAS |
| --- | --- |
| Cocaine base and acid | Cocaine base and acid |

TABLE I-continued

| NITROGEN CARRIER GAS | ZERO AIR CARRIER GAS |
| --- | --- |
| Heroin base and acid | Heroin base and acid |
| Tetrahydrocannabinol (THC) | Tetrahydrocannabinol (THC) |
| Lidocaine | Lidocaine |
| Procaine | Procaine |
| Steroids | Steroids |
| Terpenes | Terpenes |

Although the SID of the present invention can detect positive ions or easily ionized organic fragments, it is also easily adapted for use in detecting negative ions by simply switching the polarity of the bias voltage.

It has also been found that doping of the carrier gas with appropriate chemical ionization reagents may induce selective ionization by charge transfer or proton transfer mechanism in the reaction region of the SID. An example of these transfer mechanism reactions is as follows:

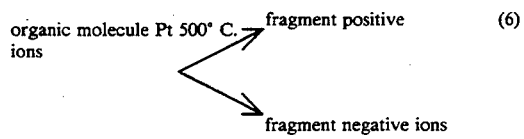

(6)

These reactions will occur with nitrogen gas or zero air carrier gas.

Therefore, by preselecting the chemical ionization reagent added to the carrier gas, the ion-molecule reaction region or surface of the platinum wire can detect specific target chemicals in a sample containing numerous chemicals.

In addition to the reaction (6), other likely reactions occurring on the surface of the platinum wire are:

(7)

where
- M is an organic molecule
- R is a reagent ion
- F is a fragment ion

In summary, the SID of the present invention is useful in detecting molecules of illicit drugs and other organic compounds while operating under zero air carrier gas conditions. Modifications are possible within the scope of this invention.

I claim:

1. A method of providing an indication of the presence of trace amounts of organic molecules in a sample, for detecting one or more of cocaine, heroine, lidocaine and procaine in their base form or salt form, and tetrahydrocannabinol, the method comprising:

i) mixing said sample in a carrier gas consisting of ambient air;

ii) directing said sample and carrier gas over a heated bare metal surface maintained at a predetermined optimum temperature;

iii) decomposing and ionizing said organic molecules present in said sample into ionized fragments, said decomposing and ionizing being effected over said heated surface;

iv) subjecting said fragments to a predetermined polarization voltage for generating respective ionization currents; and v) measuring said ionization currents to provide an indication of the presence of said organic molecules, wherein said ionized fragments are positively charged and said polarization voltage is positive, for detecting one or more of cocaine, heroin, lidocaine, and procaine in their base form or salt form, and tetrahydrocannabinol.

2. The method of claim 1, further comprising the step of scrubbing said ambient air prior to mixing with said sample so as to remove water vapour, organic contaminants and particulate matter therefrom.

3. The method of claim 1, wherein said heated surface is a platinum wire heated by conducting an electrical current therethrough.

4. The method of claim 1, further comprising the step of separating said sample into multiple constituents by means of a gas chromatograph prior directing said sample over said heated surface.

5. The method of claim 1, further comprising the step of maintaining said predetermined optimum temperature at a temperature such that optimum decomposition and ionization occurs relative to background noise in the measured ionization currents.

6. The method of claim 1, wherein said predetermined optimum temerature is in the range from 500° C. to 800° C.

7. The method of claim 1, further comprising the step of maintaining said predetermined polarization voltage in the range from 18 V to 24 V and wherein the measuring of the ionization currents includes the use of a collector electrode which is positioned such that the distance between the heated surface and said electrode is in the range from 3 to 6 millimeters.

8. The method of claim 1, further comprising the step of optimizing said predetermined optimum temperature and predetermined polarization voltage so as to optimize the sensitivity and selectivity of said surface ionization detector for detecting said substances.

9. Apparatus for detecting trace amounts of substances from vapours in a sample, said substances being characterized by organic molecules, the system comprising:

i) a surface ionization detector and ii) a source of ambient air for carrying the sample vapours into said ionization detector, wherein said detector includes a) a heated bare metal surface;

b) means for maintaining said bare metal surface at a predetermined optimum temperature, wherein said heated surface decomposes and ionizes said organic molecules present in said sample into ionized fragments at a predetermined optimum temperature and in a carrier gas consisting of ambient air;

c) means for maintaining a predetermined polarization voltage across said heated bare metal surface for subjecting said fragments to a predetermined polarization voltage and thereby generating respective ionization currents; and d) means for measuring said ionization currents to provide an indication of the presence of said organic molecules and thereby also of said substances.

10. The apparatus of claim 9, wherein said ionized fragments are positively charged and said means for maintaining a polarization voltage provides a predetermined positive voltage for detecting one or more of cocaine, heroin, lidocaine and procaine in their base form or salt form, and tetrahydrocannabinol.

11. The apparatus of claim 10, wherein said means for maintaining a polarization voltage provides a polarization voltage in the range from 18 V to 24 V;

said means for measuring said ionization currents comprises a collector electrode and the distance between said heated surface and said electrode is in the range from 3 to 6 millimeters.

12. The apparatus of claim 9, further comprising means for scrubbing said ambient air prior to use so as to remove water vapour, organic contaminants and particulate matter therefrom.

13. The apparatus of claim 9, wherein said heated surface further comprises a platinum wire heated by conducting an electrical current therethrough.

14. The apparatus of claim 9, further comprising a gas chromatograph for separating said sample into multiple constituents prior to being carried to said heated surface.

15. The apparatus of claim 14, further comprising means for directing said organic molecules and said carrier gas over said heated surface at a flow rate in the range of from 10–100 cc/min.

* * * * *